US008748558B2

(12) United States Patent
Skalla et al.

(10) Patent No.: US 8,748,558 B2
(45) Date of Patent: Jun. 10, 2014

(54) BIODEGRADABLE MACROMERS

(75) Inventors: Walter Skalla, Old Lyme, CT (US); Allison Calabrese, Memphis, TN (US); Ahmad R. Hadba, Middlefield, CT (US); Nadya Belcheva, Hamden, CT (US)

(73) Assignee: Covidien LP, Mansfield, MA (US)

( * ) Notice: Subject to any disclaimer, the term of this patent is extended or adjusted under 35 U.S.C. 154(b) by 524 days.

(21) Appl. No.: 12/594,608

(22) PCT Filed: Apr. 21, 2008

(86) PCT No.: PCT/US2008/060971
§ 371 (c)(1),
(2), (4) Date: Oct. 5, 2009

(87) PCT Pub. No.: WO2008/134276
PCT Pub. Date: Nov. 6, 2008

(65) Prior Publication Data

US 2010/0130717 A1 May 27, 2010

Related U.S. Application Data

(60) Provisional application No. 60/926,046, filed on Apr. 24, 2007.

(51) Int. Cl.
*C08G 63/00* (2006.01)
*C08G 18/00* (2006.01)

(52) U.S. Cl.
USPC ................. 528/276; 528/76; 528/79; 528/80; 528/85; 528/272; 528/274; 528/275; 528/282; 523/504; 523/512; 523/516; 560/198; 560/200

(58) Field of Classification Search
USPC ........ 528/308.2, 308.3, 308, 274, 300, 309.1, 528/371, 372, 272, 275, 276, 282; 560/198, 560/200, 201, 202; 523/504, 512, 516
See application file for complete search history.

(56) References Cited

U.S. PATENT DOCUMENTS

| | | | | |
|---|---|---|---|---|
| 4,403,093 | A * | 9/1983 | Hartman et al. | 528/297 |
| 4,425,472 | A * | 1/1984 | Howard et al. | 526/301 |
| 5,710,207 | A * | 1/1998 | Moller et al. | 524/505 |
| 6,201,060 | B1 * | 3/2001 | Jansen et al. | 524/590 |
| 6,365,637 | B1 * | 4/2002 | Zirnstein et al. | 424/439 |
| 6,395,823 | B1 | 5/2002 | Brink et al. | |
| 2003/0032734 | A1 | 2/2003 | Roby | |
| 2004/0192879 | A1 * | 9/2004 | Phelps et al. | 528/272 |
| 2005/0203268 | A1 * | 9/2005 | Wartini et al. | 528/272 |

FOREIGN PATENT DOCUMENTS

| | | | |
|---|---|---|---|
| EP | 1 719 530 | A2 | 11/2006 |
| WO | WO 2005/059003 | A1 | 6/2005 |
| WO | WO 2007/067625 | A2 | 6/2007 |

OTHER PUBLICATIONS

International Search Report for PCT/US08/60971 date of completion is Jul. 12, 2008 (2 pages).

European Search Report for EP 08746399.8-1214 date of completion is Oct. 12, 2012 (5 pages).

* cited by examiner

*Primary Examiner* — Michael L Leonard

(57) ABSTRACT

Methods for producing biocompatible compositions are provided. The biocompatible compositions include an aliphatic polyester macromer produced without the use of solvents or catalysts. The resulting aliphatic polyester macromer may be reacted with a polyisocyanate to form an end-capped aliphatic polyester macromer which, in turn, may be reacted with a polyol to produce a polyurethane. The polyurethane, in turn, may be reacted with a second polyisocyanate to produce an isocyanate-functional polyurethane. The compositions prepared by the methods of the present disclosure may be used as adhesives or sealants for medical/surgical uses.

18 Claims, No Drawings

BIODEGRADABLE MACROMERS

CROSS-REFERENCE TO RELATED APPLICATIONS

This application is a U.S. National Phase application under 35 U.S.C. §371 of PCT Application No. PCT/US2008/060971, filed on Apr. 21, 2008, which claims the benefit of and priority to U.S. Provisional Patent Application No. 60/926,046, filed Apr. 24, 2007, the entire disclosures of each of which are incorporated by reference herein.

TECHNICAL FIELD

The present disclosure relates to methods for producing biocompatible polymers capable of forming a matrix, the biocompatible polymers themselves, and the use of these polymers as surgical adhesives or sealants.

DESCRIPTION OF THE RELATED ART

In recent years there has developed increased interest in replacing or augmenting sutures with adhesive bonds. The reasons for this increased interest include: (1) the potential speed with which repair might be accomplished; (2) the ability of a bonding substance to effect complete closure, thus preventing seepage of fluids; and (3) the possibility of forming a bond without excessive deformation of tissue.

Studies in this area, however, have revealed that in order for surgical adhesives to be accepted by surgeons, they must possess a number of properties. They must exhibit high initial tack and an ability to bond rapidly to living tissue; the strength of the bond should be sufficiently high to cause tissue failure before bond failure; the adhesive should form a bridge, typically a permeable flexible bridge; and the adhesive bridge and/or its metabolic products should not cause local histotoxic or carcinogenic effects.

Several materials useful as tissue adhesives or tissue sealants are currently available. One type of adhesive that is currently available is a cyanoacrylate adhesive. However, there is the possibility that a cyanoacrylate adhesive can degrade to generate undesirable by-products such as formaldehyde. Another disadvantage with cyanoacrylate adhesives is that they can have a high flexural modulus which can limit their usefulness.

Another type of tissue sealant that is currently available utilizes components derived from bovine and/or human sources. For example, fibrin sealants are available. However, as with any natural material, variability in the material is frequently observed and, because the sealant is derived from natural proteins, there may be viral transmission concerns.

The development of synthetic biocompatible adhesives and/or sealants is ongoing. An advantage of these materials over the natural materials described above is their consistency and reduced risk of viral transmission. Methods for producing these adhesives and/or sealants frequently require the use of solvents and catalysts which, in turn, require purification steps to remove such solvents and catalysts before use. The use of these catalysts and solvents thus adds to both the time required to produce these adhesives and/or sealants as well as the costs associated with their production. It would thus be desirable to develop improved methods to produce these synthetic biological adhesives and/or sealants in a more economical fashion.

SUMMARY

The present disclosure provides methods for producing biocompatible compositions which, in turn, may be utilized as adhesives or sealants in medical and/or surgical treatments and procedures. The compositions may be produced without the use of solvents or catalysts.

In embodiments, a method of the present disclosure may include contacting a polyalkylene oxide with an aliphatic dicarboxylic acid for a period of time from about 0.5 hours to about 120 hours to form a mixture, maintaining the mixture at a temperature from about −70° C. to about 85° C., and recovering an aliphatic polyester macromer from the mixture, wherein the aliphatic polyester macromer does not possess solvent residues or catalyst residues.

In embodiments, a method of the present disclosure may include contacting a polyalkylene oxide with an aliphatic dicarboxylic acid for a period of time from about 1 hour to about 72 hours to form a mixture, maintaining the mixture at a temperature from about −10° C. to about 80° C., recovering an aliphatic polyester macromer from the mixture which does not possess solvent residues or catalyst residues, contacting the aliphatic polyester macromer with a first isocyanate including aromatic, aliphatic and alicyclic diisocyanates to produce an isocyanate end-capped aliphatic polyester macromer, and reacting the isocyanate end-capped aliphatic polyester macromer with a polyol to produce a polyurethane as the biocompatible composition.

In some embodiments, the aliphatic polyester macromer thus obtained may be reacted with a polyisocyanate to form an end-capped aliphatic polyester macromer which, in turn, may be reacted with a polyol to produce a polyurethane. The polyurethane, in turn, may be reacted with a second polyisocyanate to produce an isocyanate-functional polyurethane.

DETAILED DESCRIPTION

The present disclosure relates to compounds suitable for forming a bioabsorbable composition which may be used as a tissue adhesive or sealant.

The methods of the present disclosure may be utilized to produce hydroxy-terminated polyalkylene oxide based esters, oligoesters and/or polyesters, and methods for their production. In embodiments, these esters, oligoesters and/or polyesters, sometimes referred to herein as aliphatic polyester macromers, may be produced by way of a condensation reaction without utilizing catalysts or solvents.

The aliphatic polyester macromers thus produced may then be reacted with a first diisocyanate to produce an isocyanate end-capped macromer. The isocyanate end-capped macromer may then be reacted with a polyol to produce a polyurethane. The resulting polyurethane may then be reacted with a second polyisocyanate to produce an isocyanate-functional polyurethane. The polyurethane or isocyanate-functional polyurethane may be utilized in vivo as an adhesive, sealant, drug delivery device, and the like.

The compositions of the present disclosure are not solid at the temperatures encountered in use, but rather, are flowable. Flowable materials have a measurable viscosity. For example, the present compounds may have a viscosity of from about 1,000 to about 300,000 centipoise ("cP") at temperatures of from about 0° C. to about 40° C.

In embodiments, a polyalkylene oxide may be utilized to form the aliphatic polyester macromer. Suitable polyalkylene oxides which may be utilized to form the aliphatic polyester macromers include polyethylene oxide ("PEO"), polypropylene oxide ("PPO"), and block or random copolymers of polyethylene oxide (PEO) and polypropylene oxide (PPO), including triblock PEO-PPO copolymers commercially available as PLURONICS® from BASF Corporation (Mt. Olive, N.J.). In embodiments, a polyethylene glycol ("PEG")

may be utilized as the polyalkylene oxide. It may be desirable to utilize a PEG with a molecular weight of from about 200 to about 1000, in embodiments from about 400 to about 900. Suitable PEGs include those commercially available from a variety of sources under the designations PEG 200, PEG 400, PEG 600 and PEG 900.

In other embodiments, suitable polyalkylene oxides include polyethylene glycol/polypropylene glycol copolymers. In some embodiments, a copolymer including about 17 moles polyethylene glycol to about 6 moles polypropylene glycol (17PEG/6PPG), commercially available as UCON 75H450 from Dow Chemical (Union Carbide), may be utilized.

The above polyalkylene oxides may be combined with aliphatic dicarboxylic acids or their reactive derivatives to form the aliphatic polyester macromers of the present disclosure. Suitable aliphatic dicarboxylic acids include those having from about 2 to about 8 carbon atoms, such as sebacic acid, azelaic acid, suberic acid, pimelic acid, adipic acid, glutaric acid, succinic acid, malonic acid, oxalic acid and combinations thereof. Suitable derivatives of the aliphatic dicarboxylic acids include, for example, oxalyl chloride, malonyl chloride, succinyl chloride, glutaryl chloride, adipoyl chloride, suberoyl chloride, pimeloyl chloride, sebacoyl chloride, and/or combinations thereof. As used herein, an aliphatic dicarboxylic acid includes both the diacids and derivatives thereof described above.

The amounts of polyalkylene oxide and aliphatic dicarboxylic acid used to form the aliphatic polyester macromer may depend, in embodiments, on the desired properties of the resulting composition, for example, whether it is to be utilized in forming an adhesive, sealant, drug delivery device, etc. The amount of polyalkylene oxide utilized to form the aliphatic polyester macromer may be from about 2.2 to about 1.1 molar ratio of polyalkylene oxide to aliphatic dicarboxylic acid, in embodiments from about 2.0 to about 1.4 molar ratio of polyalkylene oxide to aliphatic dicarboxylic acid.

The polyalkylene oxide and aliphatic dicarboxylic acid may be combined in any order. In some embodiments, the components may be combined at one time; in other embodiments the components may be combined over a period of time, for example by dropwise addition of one component to the other, for a period of time of from about 10 seconds to about 8 hours, in embodiments from about 10 minutes to about 3 hours.

The combination of the two components may be held at a suitable temperature, in embodiments from about −70° C. to about 85° C., in embodiments from about −10° C. to about 80° C., in other embodiments from about 20° C. to about 75° C., for a period of time of from about 0.5 hours to about 120 hours, in embodiments from about 1 hour to about 72 hours. In some embodiments the two components may be held at a suitable temperature for a period of time from about 0.5 hours to about 5 hours.

In some embodiments, it may be desirable to utilize mechanical agitation to assist in combining the polyalkylene oxide and aliphatic dicarboxylic acid. Any method within the purview of those skilled in the art may be utilized including, for example, blending, mixing, stirring, and the like. Blending, mixing, stirring, etc., may take place for a period of time from about 1 hour to about 72 hours, in embodiments from about 12 hours to about 24 hours, at a temperature of from about 20° C. to about 75° C., in embodiments from about 30° C. to about 60° C. Mixing and/or blending and/or stirring may occur at speeds from about 50 revolutions per minute (rpm) to about 1000 rpm, in embodiments from about 150 rpm to about 600 rpm.

In embodiments, the two components may be combined in the presence of an inert gas or under an inert atmosphere, such as nitrogen.

In some embodiments, heating the two components and subjecting them to nitrogen while stirring may result in an increase in the pH of the reaction mixture from a starting pH of from about 0 to about 2 to a final pH of from about 3 to about 7, in embodiments from about 4 to about 6. In embodiments, an inert gas such as nitrogen may be bubbled through the two components while stirring.

In some embodiments, an acid scavenger may be added to assist in raising the pH of the reaction mixture. Suitable acid scavengers include, for example, chitosan, neutral and basic alumina, cross-linked polystyrene-aminomethylated ion exchange resins, activated charcoal, combinations thereof, and the like.

The resulting aliphatic polyester macromer may then be recovered from the reaction mixture utilizing any method within the purview of those skilled in the art, including filtration, centrifugation, and the like. For example, in embodiments, the reaction mixture may be filtered to remove any acid scavengers. In other embodiments, the aliphatic polyester macromer may be precipitated from the reaction mixture by the addition of an ether such as ethyl ether or petroleum ether, and then collected by suitable means which can include decanting, filtration, and the like. Other methods suitable for recovering the present compounds will be apparent to those skilled in the art. In embodiments, the resulting aliphatic polyester macromer may be neutralized to a pH of about 7 by treating with alumina, which may be either neutral or basic. While not necessary, this treatment may occur in the presence of a solvent, such as tetrahydrofuran, chloroform, methylene chloride, dioxane, dimethylformamide (DMF), dimethylsulfoxide (DMSO), ethanol, isopropanol, methanol, acetonitrile, and the like, with the neutralized product being recovered after filtration, solvent evaporation (where solvent is utilized), and/or precipitation, such as in an ether including petroleum ether or diethyl ether. The aliphatic polyester macromer obtained may then be subjected to washing and drying, such as by vacuum drying.

In accordance with the present disclosure, the aliphatic polyester macromer may be formed without the use of a catalyst or a solvent. Thus, compositions of the present disclosure need not be subjected to costly and time-consuming purification steps that conventional processes, including those which utilize catalysts and solvents, may require. As the resulting aliphatic polyester macromer lacks residues of such solvents and/or catalysts, the compounds of the present disclosure may produce less inflammation when used in vivo compared with compounds produced by conventional methods utilizing catalysts and/or solvents.

The polyalkylene oxide utilized may be present in an amount from about 60% by weight to about 95% by weight of the aliphatic polyester macromer, in embodiments from about 80% by weight to about 93% by weight of the aliphatic polyester macromer. Thus, the aliphatic or aromatic dicarboxylic acids or their reactive derivatives may be present in an amount from about 5% by weight to about 40% by weight of the aliphatic polyester macromer, in embodiments from about 7% by weight to about 20% by weight of the aliphatic polyester macromer. In some embodiments, the aliphatic polyester macromer may be formed by combining adipoyl chloride with a PEG such as PEG 600 or a polyethylene glycol/polypropylene glycol copolymer.

In embodiments, the resulting aliphatic polyester macromer is of the following formula:

$$HO—(R-A)_n-R—OH \quad (I)$$

wherein A is a group derived from the aliphatic dicarboxylic acid or derivative; R can be the same or different at each occurrence and is a group derived from the polyalkylene oxide; and n is a number from about 1 to about 10, in embodiments from about 2 to about 7. In embodiments, the A group can be derived from adipic acid or a derivative thereof, such as adipoyl chloride, and R can be derived from a polyethylene glycol having a molecular weight of less than about 1,000. In other embodiments, the A group can be derived from adipic acid or a derivative thereof, such as adipoyl chloride, and R can be derived from a polyethylene glycol/polypropylene glycol copolymer.

The molecular weight and viscosity of these compounds will depend on a number of factors such as the particular diacid used, the particular polyalkylene oxide used and the number of repeat units present. Generally, the viscosity of these compounds may be from about 100 to about 10,000 cP at 25° C. and a shear rate of from about 3 $sec^{-1}$ to about 25 $sec^{-1}$.

These compounds may be useful for a number of applications. For example, they may be used to produce compounds capable of cross-linking to form a gel matrix that serves as an excellent tissue adhesive or sealant.

For adhesive or sealant applications, it may be desirable to endcap the above aliphatic polyester macromer to provide a reactive end group. Suitable reactive end groups include amine reactive end groups, for example, isocyanate groups, isothiocyanates, diimidazoles, imidoesters, hydroxysuccinimide esters, and aldehydes. Methods for endcapping the aliphatic polyester macromer to provide a reactive end group are within the purview of those skilled in the art. For example, the aliphatic polyester macromer may be reacted with an aliphatic or aromatic diisocyanate to produce a diisocyanate-functional compound. Suitable isocyanates for endcapping the aliphatic polyester macromer include aromatic, aliphatic and alicyclic isocyanates. Examples include, but are not limited to, aromatic diisocyanates such as 2,4-toluene diisocyanate, 2,6-toluene diisocyanate, 2,2'-diphenylmethane diisocyanate, 2,4'-diphenylmethane diisocyanate, 4,4'-diphenylmethane diisocyanate, diphenyldimethylmethane diisocyanate, dibenzyl diisocyanate, naphthylene diisocyanate, phenylene diisocyanate, xylylene diisocyanate, 4,4'-oxybis(phenylisocyanate) or tetramethylxylylene diisocyanate; aliphatic diisocyanates such as tetramethylene diisocyanate, hexamethylene diisocyanate, dimethyl diisocyanate, lysine diisocyanate, 2-methylpentane-1,5-diisocyanate, 3-methylpentane-1,5-diisocyanate or 2,2,4-trimethylhexamethylene diisocyanate; and alicyclic diisocyanates such as isophorone diisocyanate, cyclohexane diisocyanate, hydrogenated xylylene diisocyanate, hydrogenated diphenylmethane diisocyanate, hydrogenated trimethylxylylene diisocyanate, 2,4,6-trimethyl 1,3-phenylene diisocyanate or commercially available DESMODURS® from Bayer Material Science, as well as combinations of the foregoing diisocyanates.

The ratio of diisocyanate to the aliphatic polyester macromer can be from about 1:1 to about 10:1 molar ratio, in embodiments from about 2:1 to about 6:1 molar ratio. In some embodiments, the ratio of diisocyanate to the aliphatic polyester macromer can be from about 2:1 to about 4:1.

In accordance with the present disclosure, the diisocyanate and the aliphatic polyester macromer may be combined and the end-capping reaction is allowed to proceed. The diisocyanate and the aliphatic polyester macromer can be combined by any means within the purview of those skilled in the art, including mixing and/or stirring. In embodiments, the diisocyanate and the aliphatic polyester macromer may be combined by stirring for a period of time of from about 1 hour to about 24 hours, in embodiments from about 2 hours to about 18 hours, in other embodiments from about 3 hours to about 8 hours. The diisocyanate and the aliphatic polyester macromer can be heated, to enhance the rate of the end-capping reaction, to a temperature of from about 40° C. to about 140° C., in embodiments from about 50° C. to about 130° C., in other embodiments from about 60° C. to about 120° C.

In some embodiments, the diisocyanate and the aliphatic polyester macromer may be mixed under an inert atmosphere, such as nitrogen.

It should be understood that more than one different aliphatic polyester macromer can be endcapped in a single reaction. For example, an aliphatic polyester macromer of the above-mentioned formula (I) wherein n is 3 can be prepared and combined with an aliphatic polyester macromer of the above-mentioned formula (I) wherein n is 5 that had been separately prepared. The mixture of aliphatic polyester macromers can then be endcapped to provide macromers possessing a reactive group in a single reaction. The resulting product will be a mixture of diisocyanate-functional compounds of the formula shown above.

The resulting diisocyanate-functional compounds of the present disclosure may be of the following formula:

$$OCN—X—HNCOO—(R-A)_n-R—OOCNH—X—NCO \quad (II)$$

wherein X is an alicyclic, aliphatic or aromatic group; A is a group derived from an aliphatic dicarboxylic acid or derivative thereof; R can be the same or different at each occurrence and is a group derived from a polyalkylene oxide; and n is a number from about 1 to about 10, in embodiments from about 2 to about 7. In some embodiments, X may be derived from toluene, hexamethylene, tetramethylene, lysine, ethylated lysine isophorone, xylene, diphenylmethane, diphenyidimethylmethane, dibenzyl diisocyanate, oxybis(phenylisocyanate), tetramethylxylylene or optionally mixtures thereof or combinations thereof. The NCO content of the diisocyanate-functional compound can vary from about 2% to about 10%, in embodiments from about 3% to about 6%. The viscosity of these diisocyanate-functional compounds will depend on a number of factors such as the particular diisocyanate used, the particular diacid used, the particular polyalkylene oxide used, and the number of repeat units present. In embodiments, the viscosity of these compounds may be from about 500 to about 50,000 cP at 25° C.

The above isocyanate-functional compound may then be utilized to form a composition of the present disclosure suitable for use as an adhesive or sealant.

In other embodiments, after the end-capping reaction has occurred, a polyol can be added and allowed to react with the free isocyanate group(s) of the diisocyanate end-capped aliphatic polyester macromer. Suitable polyols which may react with the free isocyanate of the diisocyanate end-capped aliphatic polyester macromer include, but are not limited to, polyhydric alcohols such as ethylene glycol, diethylene glycol, triethylene glycol, polyethylene glycol ("PEG"), PEG adipate, propylene glycol, dipropylene glycol, polypropylene glycol ("PPG"), tetraethylene glycol, 1,3-butanediol, 1,4-butanediol, 1,2,4-butanetriol, glycerol, trimethylol propane, 1,2,5-hexanetriol, 1,2,6-hexanetriol, polycaprolactone triol, polylactide triol, 4,4'-dihydroxyphenylpropane, 4,4'-dihydroxyphenylmethane, bis (hydroxyethyl)terephthalate, cyclohexane dimethanol, furan dimethanol, pentaerythritol, glucose, sucrose, sorbitol, cyclodextrins, and the reaction products of such polyols with propylene oxide and/or ethylene oxide. Other polyols which may be utilized include poloxamers such as polyethylene oxide (PEO) copolymers with polypropylene oxide (PPO) such as the triblock PEO-PPO copolymers commercially available as PLURONICS® from BASF Corporation (Mt. Olive, N.J.). Combinations of the foregoing polyols may be utilized in embodiments. The result of this reaction is a polyurethane.

The polyol may have a weight average molecular weight ranging from about 50 to about 5000, in embodiments from about 100 to about 3000, and a functionality of from about 2 to about 6.

In other embodiments, a polyethylene glycol may be utilized as the polyol. The molecular weight of the polyethylene glycol utilized as the polyol can vary depending upon the intended end use of the biocompatible composition, i.e., adhesive or sealant. In some embodiments, the molecular weight of the PEG utilized as the polyol can be from about 100 to about 20,000, in embodiments from about 500 to about 10,000, in other embodiments from about 1,000 to about 5,000.

The molar ratio of diisocyanate end-capped aliphatic polyester macromer to polyol can be from about 1:1 to about 50:1, in embodiments from about 2:1 to about 25:1, in other embodiments from about 3:1 to about 20:1.

In one embodiment, the polyol and the isocyanate end-capped aliphatic polyester macromer can be combined by stirring for a period of time of from about 1 to about 360 hours, in embodiments from about 2 to about 240 hours, in other embodiments from about 3 to about 168 hours.

The polyol and the isocyanate end-capped aliphatic polyester macromer can be heated to enhance the rate of the functionalizing reaction at a temperature of from about 40° C. to about 100° C., in embodiments from about 50° C. to about 85° C., in other embodiments from about 55° C. to about 75° C.

In embodiments the polyol, having multiple hydroxyl groups suitable for reacting with an isocyanate, may function as a branching agent. In embodiments, separate branching agents may be added. Such branching agents are within the purview of those skilled in the art.

As those skilled in the art will appreciate, a mixture of compounds having various degrees of functionality may result from reacting the diisocyanate-functional compound with the polyol. For example, one diisocyanate-functional compound may react with the polyol to provide a compound with a single isocyanate functionality; or two diisocyanate-functional compounds may react with a single polyol to provide a compound with two isocyanate functionalities; or three diisocyanate-functional compounds may react with a single polyol to provide a compound with a three isocyanate functionalities; or two polyols may react with a single diisocyanate-functional compound to provide a compound with no isocyanate functionalities. Those skilled in the art will envision other possible reaction products that may form.

It should be understood that more than one diisocyanate-functional compound can be reacted with a polyol in a single reaction. For example, an aliphatic polyester macromer of the above-mentioned formula (I) wherein n is 3 can be prepared and combined with an aliphatic polyester macromer of the above-mentioned formula (I) wherein n is 5 that had been separately prepared. The mixture of aliphatic polyester macromers can then be endcapped to provide a reactive group in a single reaction. The resulting mixture of diisocyanate-functional compounds can then be reacted with a polyol. As another example, an aliphatic polyester macromer of the above-mentioned formula (I) wherein n is 3 can be prepared and endcapped and an aliphatic polyester macromer of the above-mentioned formula (I) wherein n is 5 can be separately prepared and endcapped. The two diisocyanate-functional compounds can then be mixed. The resulting mixture of diisocyanate-functional compounds can then be reacted with a polyol in a single reaction.

The resulting polyurethane may be utilized as an adhesive, sealant, medical device, drug delivery device, and the like.

In embodiments, after the reaction of the polyol with the free isocyanate of the diisocyanate end-capped aliphatic polyester macromer is completed, a second polyisocyanate may be added to the resulting polyurethane and allowed to react with the free hydroxyl end groups of the polyol on the polyurethane. Suitable isocyanates which may be utilized as the second polyisocyanate to further functionalize these polyurethanes by reacting with their free hydroxy end groups include those described above for producing the isocyanate-functional aliphatic polyester macromer. In embodiments, diisocyanates such as toluene diisocyanate (TDI), 4,4'-diphenylmethane diisocyanate (MDI), 2,4,6-trimethyl-1,3 phenylene diisocyanate, 1,6-hexamethylene diisocyanate (HMDI) and isophorone diisocyanate (IPDI) may be utilized as the second isocyanate to further functionalize these hydroxy end groups. An aliphatic diisocyanate, such as hexamethylene diisocyanate, can be useful in some embodiments.

The ratio of second diisocyanate to polyurethane can be from about 2:1 to about 20:1, in embodiments from about 2.25:1 to about 10:1, in other embodiments from about 2.5:1 to about 4:1.

In embodiments, the second diisocyanate and the polyurethane may be combined by stirring for a period of time of from about 1 hour to about 24 hours, in other embodiments from about 2 to about 18 hours, in yet other embodiments from about 3 to about 8 hours.

The second diisocyanate and polyurethane can be heated to enhance the rate of the end-capping reaction at a temperature of from about 40° C. to about 140° C., in embodiments from about 50° C. to about 120° C., in other embodiments from about 60° C. to about 100° C.

In some cases the reaction of the polyol with free isocyanates on the isocyanate end-capped aliphatic polyester macromer to form a polyurethane, and the reaction of the polyurethane with additional polyisocyanate occurs, at least in part, simultaneously.

The resulting isocyanate-functional polyurethane may be linear or can have a branched or star configuration. The molecular weight of the isocyanate-functional polyurethane can be from about 500 to about 50,000, in embodiments from about 1000 to about 20,000, in other embodiments from about 2000 to about 10,000.

The resulting isocyanate-functional polyurethane may then be utilized to form an adhesive or sealant.

In embodiments, the polyurethane or the aliphatic polyester macromer may also possess at least one bioabsorbable group to alter the degradation profile of the resulting compound. Bioabsorbable groups which may be present include, for example groups derived from glycolide, glycolic acid, lactide, lactic acid, caprolactone, dioxanone, trimethylene carbonate, and combinations thereof. For example, in one embodiment the polyol may include trimethylol propane in combination with dioxanone and glycolide. Methods for adding bioabsorbable groups are within the purview of those skilled in the art.

Upon administration to tissue in situ, the polyurethane and/or functionalized compounds described hereinabove may cross-link to form a gel matrix that may serve as an excellent tissue adhesive or sealant. In embodiments, the cross-linking reaction may be conducted at temperatures of from about 20° C. to about 40° C., for a period of time of from about fifteen seconds to about 20 minutes, in embodiments from about 1 minute to about 10 minutes.

The compounds described hereinabove can be used alone or can be formulated into compositions. The concentrations of the components utilized to form the compositions will vary depending upon a number of factors, including the types and molecular weights of the particular components used and the desired end use application of the biocompatible composition, e.g., an adhesive or sealant. In embodiments, the composition may contain from about 0.5% to about 100% of the previously described functionalized polyester macromer. Where the functionalized polyester macromer has been reacted with a branching agent, the composition may contain from about 0.1 to about 15% of the branching agent by weight.

While prior methods may utilize solvents and/or catalysts in forming similar materials (see, for example, U.S. Patent Application Publication No. 2006/0253094, the entire disclosure of which is incorporated by reference herein), the adhesives and/or sealants in accordance with the present disclosure may be prepared without any additional solvent or catalyst.

In some embodiments, water may also be added to the composition to decrease cure time. When added, water should be introduced at or near the time of use of the composition to avoid unwanted or pre-mature crosslinking. Generally, the amount of water may be from about 1 to about 50 weight percent based on the entire composition.

A variety of optional ingredients may also be added to the biocompatible compositions of the present disclosure, including but not limited to, bioactive agents, medicinal agents, and the like. In some embodiments, the present compositions may optionally contain one or more bioactive agents. The term "bioactive agent", as used herein, is used in its broadest sense and includes any substance or mixture of substances that have clinical use. Consequently, bioactive agents may or may not have pharmacological activity per se, e.g., a dye. Alternatively a bioactive agent could be any agent which provides a therapeutic or prophylactic effect, a compound that affects or participates in tissue growth, cell growth, cell differentiation, a compound that may be able to invoke a biological action such as an immune response, or could play any other role in one or more biological processes.

Examples of classes of bioactive agents which may be utilized in accordance with the present disclosure include antimicrobials, analgesics, antipyretics, anesthetics, antiepileptics, antihistamines, anti-inflammatories, cardiovascular drugs, diagnostic agents, sympathomimetics, cholinomimetics, antimuscarinics, antispasmodics, hormones, growth factors, muscle relaxants, adrenergic neuron blockers, antineoplastics, immunogenic agents, immunosuppressants, gastrointestinal drugs, diuretics, steroids, lipids, lipopolysaccharides, polysaccharides, and enzymes. It is also intended that combinations of bioactive agents may be used.

Suitable antimicrobial agents which may be included as a bioactive agent in the present compositions include triclosan, also known as 2,4,4'-trichloro-2'-hydroxydiphenyl ether, chlorhexidine and its salts, including chlorhexidine acetate, chlorhexidine gluconate, chlorhexidine hydrochloride, and chlorhexidine sulfate, silver and its salts, including silver acetate, silver benzoate, silver carbonate, silver citrate, silver iodate, silver iodide, silver lactate, silver laurate, silver nitrate, silver oxide, silver palmitate, silver protein, and silver sulfadiazine, polymyxin, tetracycline, aminoglycosides, such as tobramycin and gentamicin, rifampicin, bacitracin, neomycin, chloramphenicol, miconazole, quinolones such as oxolinic acid, norfloxacin, nalidixic acid, pefloxacin, enoxacin and ciprofloxacin, penicillins such as oxacillin and pipracil, nonoxynol 9, fusidic acid, cephalosporins, and combinations thereof. In addition, antimicrobial proteins and peptides such as bovine or rh-lactoferrin and lactoferricin B may be included as a bioactive agent in the present compositions.

Other bioactive agents which may be included as a bioactive agent in the present compositions include: local anesthetics; non-steroidal antifertility agents; parasympathomimetic agents; psychotherapeutic agents; tranquilizers; decongestants; sedative hypnotics; steroids; sulfonamides; sympathomimetic agents; vaccines; vitamins; antimalarials; anti-migraine agents; anti-parkinson agents such as L-dopa; anti-spasmodics; anticholinergic agents (e.g.

oxybutynin); antitussives; bronchodilators; cardiovascular agents such as coronary vasodilators and nitroglycerin; alkaloids; analgesics; narcotics such as codeine, dihydrocodeinone, meperidine, morphine and the like; non-narcotics such as salicylates, aspirin, acetaminophen, d-propoxyphene and the like; opioid receptor antagonists, such as naltrexone and naloxone; anti-cancer agents; anti-convulsants; anti-emetics; antihistamines; anti-inflammatory agents such as hormonal agents, hydrocortisone, prednisolone, prednisone, non-hormonal agents, allopurinol, indomethacin, phenylbutazone and the like; prostaglandins and cytotoxic drugs; estrogens; antibacterials; antibiotics; anti-fungals; anti-virals; anticoagulants; anticonvulsants; antidepressants; antihistamines; and immunological agents.

Other examples of suitable bioactive agents which may be included in the present compositions include viruses and cells, peptides, polypeptides and proteins, analogs, muteins, and active fragments thereof, such as immunoglobulins, antibodies, cytokines (e.g. lymphokines, monokines, chemokines), blood clotting factors, hemopoietic factors, interleukins (IL-2, IL-3, IL-4, IL-6), interferons (beta-IFN, (alpha-IFN and gamma-IFN), erythropoietin, nucleases, tumor necrosis factor, colony stimulating factors (e.g., GCSF, GM-CSF, MCSF), insulin, anti-tumor agents and tumor suppressors, blood proteins, gonadotropins (e.g., FSH, LH, CG, etc.), hormones and hormone analogs (e.g., growth hormone), vaccines (e.g., tumoral, bacterial and viral antigens); somatostatin; antigens; blood coagulation factors; growth factors (e.g., nerve growth factor, insulin-like growth factor); protein inhibitors, protein antagonists, and protein agonists; nucleic acids, such as antisense molecules, DNA and RNA; oligonucleotides; and ribozymes.

Naturally occurring polymers, including proteins such as collagen and derivatives of various naturally occurring polysaccharides such as glycosaminoglycans, can optionally be incorporated into the compositions of the present disclosure as the bioactive agent.

Imaging agents such as iodine or barium sulfate, or fluorine, can also be combined with the compositions of the present disclosure to allow visualization of the surgical area through the use of imaging equipment, including X-ray, MRI, and CAT scan equipment.

Additionally, an enzyme may be added to the biocompatible compositions of the present disclosure to increase their rate of degradation. Suitable enzymes include, for example, peptide hydrolases such as elastase, cathepsin G, cathepsin E, cathepsin B, cathepsin H, cathepsin L, trypsin, pepsin, chymotrypsin, γ-glutamyltransferase (γ-GTP) and the like; sugar chain hydrolases such as phosphorylase, neuraminidase, dextranase, amylase, lysozyme, oligosaccharase and the like;

oligonucleotide hydrolases such as alkaline phosphatase, endoribonuclease, endodeoxyribonuclease and the like. In some embodiments, where an enzyme is added, the enzyme may be included in a liposome or microsphere to control the rate of its release, thereby controlling the rate of degradation of the adhesive composition of the present disclosure. Methods for incorporating enzymes into liposomes and/or microspheres are within the purview of those skilled in the art.

In addition, at least one linkage that is hydrolytically or enzymatically degradable may be incorporated into the isocyanate-functional polyurethane. Linkages that are hydrolytically degradable include, but are not limited to, esters, anhydrides, and phosphoesters. Linkages which are enzymatically degradable include, but are not limited to: an amino acid residue such as -Arg-, -Ala-, -Ala(D)-, -Val-, -Leu-, -Lys-, -Pro-, -Phe-, -Tyr-, -Glu-, and the like; 2-mer to 6-mer oligopeptides such as -Ile-Glu-Gly-Arg-, -Ala-Gly-Pro-Arg-,-Arg-Val-$(Arg)_2$-, -Val-Pro-Arg-, -Gln-Ala-Arg-, -Gln-Gly-Arg-, -Asp-Pro-Arg-,-Gln$(Arg)_2$ -, Phe-Arg-, -$(Ala)_3$-, -$(Ala)_2$-, -Ala-Ala(D)-, -$(Ala)_2$-Pro-Val-, -$(Val)_2$-,-$(Ala)_2$-Leu-, -Gly-Leu-, -Phe-Leu-, -Val-Leu-Lys-, -Gly-Pro-Leu-Gly-Pro-, -$(Ala)_2$-Phe-, -$(Ala)_2$-Tyr-, -$(Ala)_2$-His-, -$(Ala)_2$-Pro-Phe-, -Ala-Gly-Phe-, -Asp-Glu-, -$(Glu)_2$ -, -Ala-Glu-, -Ile-Glu-, -Gly-Phe-Leu-Gly-, -$(Arg)_2$-; D-glucose, N-acetylgalactosamine, N-acetylneuraminic acid, N-acetylglucosamine, N-acetylmannnosamine or the oligosaccharides thereof; oligodeoxyribonucleic acids such as oligodeoxyadenine, oligodeoxyguanine, oligodeoxycytosine, and oligodeoxythymidine; oligoribonucleic acids such as oligoadenine, oligoguanine, oligocytosine, oligouridine, and the like. Those skilled in the art will readily envision reaction schemes for incorporating enzymatically degradable linkages into the isocyanate-functional polyurethane.

A single bioactive agent may be added to the present compositions or, in alternate embodiments, any combination of bioactive agents may be added to the present compositions.

Due to the presence of the functionalized compounds described hereinabove, the present compositions cross-link to form a gel matrix that serves as an excellent tissue adhesive or sealant. Normally, the cross-linking reaction may be conducted at temperatures of from about 20° C. to about 40° C., for a period of time of from about 15 seconds to about 20 minutes, in embodiments from about 30 seconds to about 10 minutes. The exact reaction conditions for achieving cross-linking of the compositions of the present disclosure depend upon a variety of factors, including the functionality of the compound, the degree of endcapping, the degree of functionalization, and the like.

The compositions produced by these methods are biocompatible and non-immunogenic. The biocompatible compositions can be applied to living tissue and/or flesh of animals, including humans.

While certain distinctions may be drawn between the usage of the terms "flesh" and "tissue" within the scientific community, the terms are used interchangeably herein as referring to a general substrate upon which those skilled in the art would understand the present bioabsorbable composition to be utilized within the medical field for the treatment of patients. As used herein, "tissue" may include, but is not limited to, skin, bone, neuron, axon, cartilage, blood vessel, cornea, muscle, fascia, brain, prostate, breast, endometrium, lung, pancreas, small intestine, blood, liver, testes, ovaries, cervix, colon, stomach, esophagus, spleen, lymph node, bone marrow, kidney, peripheral blood, embryonic and/or ascite tissue.

The biocompatible compositions of the present disclosure can be used for a number of different human and animal medical applications including, but not limited to, wound closure (including surgical incisions and other wounds), adhesives for adhering medical devices (including implants) to tissue, sealants and void fillers, and embolic agents. Adhesives may be used to bind tissue together either as a replacement of, or as a supplement to, sutures, staples, tapes and/or bandages. Use of the biocompatible composition as an adhesive can eliminate or substantially reduce the number of sutures normally required during current practices, and eliminate the subsequent need for removal of staples and certain types of sutures. The disclosed biocompatible composition as an adhesive can thus be particularly suitable for use with delicate tissues where sutures, clamps or other conventional tissue closure mechanisms may cause further tissue damage.

Additional applications include use of the biocompatible compositions as sealants for sealing tissues to prevent or control blood or other fluid leaks both during and after a surgical procedure. The compositions may also be used to prevent or control blood or other fluid leaks at suture or staple lines. The compositions of the present disclosure can also be applied to prevent air leaks associated with pulmonary surgery. Compounds herein may be applied directly to the desired area in at least an amount sufficient to seal off any defect in the tissue and seal off any fluid or air movement.

In another embodiment, the biocompatible compositions can be used to attach skin grafts and position tissue flaps during reconstructive surgery. In still another embodiment, the biocompatible compositions can be used to close tissue flaps in periodontal surgery.

To effectuate the joining of two tissue edges, the two edges are approximated and the biocompatible composition of the present disclosure, i.e., the isocyanate-functional aliphatic polyester macromer, and/or the isocyanate-functional polyurethane, may be applied thereto. The composition then crosslinks. In this case the biocompatible composition of the present disclosure can be used as an adhesive to close a wound, including a surgical incision. The biocompatible composition of the present disclosure can thus be applied to the wound and allowed to set, thereby closing the wound.

Application of the compositions of the present disclosure can be done by any conventional means. These include dripping, brushing, or other direct manipulation of the compositions on the tissue surface, or spraying of the compositions onto the surface. The biocompatible composition can also be dispensed from a conventional adhesive dispenser. In open surgery, application by hand, forceps or the like is contemplated. In endoscopic surgery, the compositions can be delivered through the cannula of a trocar, and spread at the site by any device known in the art.

In other embodiments, especially where a composition of the present disclosure is to be utilized as a void filler or sealant to fill a defect in an animal's body, it may be advantageous to more precisely control the conditions and extent of cross-linking. For example, it may be desirable to partially cross-link the composition prior to use to fill a void in animal tissue. In such a case composition of the present disclosure can be applied to the void or defect and allowed to set, thereby filling the void or defect.

In other embodiments, the present disclosure is directed to a method for using compounds of the present disclosure to adhere a medical device to tissue. The medical device may include an implant. Other medical devices include, but are not limited to, pacemakers, stents, shunts and the like. Generally, for adhering a device to the surface of animal tissue, a composition of the present disclosure can be applied to the device, to the tissue surface, or to both. The device and tissue surface are then brought into contact with the present composition there between. Once the composition crosslinks and sets, the device and tissue surface are effectively adhered to each other.

The present compositions can also be used to prevent post surgical adhesions. In such an application, a composition of the present disclosure is applied and cured to form a layer on surfaces of internal tissues in order to prevent the formation of adhesions at a surgical site during the healing process.

Where the bioabsorbable composition is intended for delivery of a drug or protein, the amounts of the compounds of the present disclosure can be adjusted to promote the initial retention of the drug or polymer in the bioabsorbable composition and its subsequent release. Methods and means for making such adjustments will be readily apparent to those skilled in the art.

When used as a sealant, the biocompatible composition of the present disclosure can be used in surgery to prevent or inhibit bleeding or fluid leakage both during and after a surgical procedure. It can also be applied to prevent air leaks associated with pulmonary surgery. The isocyanate-functional polyurethane may be applied directly to the desired area in at least an amount necessary to seal off any defect in the tissue and seal off any fluid or air movement.

The compositions prepared by the methods of the present disclosure have a number of advantageous properties. The biocompatible composition rapidly forms a compliant gel matrix, which insures stationary positioning of tissue edges or implanted medical devices in the desired location and lowers overall required surgical/application time. The biocompatible composition exhibits low swelling upon gel matrix formation, and therefore retains the positional integrity of the aligned tissue edges and/or location of a medical device.

The biocompatible composition of the present disclosure forms strong cohesive bonds. It exhibits excellent mechanical performance and strength, while retaining the necessary pliability to adhere living tissue. This strength and pliability allows a degree of movement of tissue without shifting the surgical tissue edge. Additionally, the biocompatible composition can be biodegradable where hydrolytically bioabsorbable groups or enzymatic linkages are included, allowing the degradation components to pass safely through the subject's body.

The resulting biocompatible compositions of the present disclosure are safe, possess enhanced adherence to tissue, have enhanced stability, are biocompatible, have hemostatic potential, have low cost, and are easy to prepare and use. By varying the selection of the polymer components, the strength and elasticity of the biocompatible composition can be controlled, as can the gelation time. As these compositions are prepared without catalysts or solvents, the methods of the present disclosure are less expensive and simpler as fewer components are necessary for producing the biocompatible compositions and purification steps are not required. Moreover, the compositions of the present disclosure produce little or no inflammation upon use in vivo.

Compositions of the present disclosure may be purified and/or sterilized utilizing any method within the purview of those skilled in the art. Such methods include, for example, sterilization techniques such as gamma-irradiation, e-beam, low temperature gas plasma, vapor phase hydrogen peroxide, combinations thereof, and the like. (See, e.g., Simmons et al., Biomaterials 27 (2006), pp. 4484-4497.)

In order that those skilled in the art may be better able to practice the features of the present disclosure described herein, the following examples are provided to illustrate, but not limit, the features of the present disclosure.

EXAMPLES

Example 1

About 26 grams of UCON™ lubricant 75-H-450, a polyethylene glycol/polypropylene glycol copolymer (about 17 moles polyethylene glycol to about 6 moles polypropylene glycol (17PEG/6PPG)) from the Dow Chemical Company, was combined with about 3 grams of adipoyl chloride (ClOC $(CH_2)_4$COCl, sometimes referred to herein as AdCl) (98%, Sigma Aldrich, St. Louis, Mo.) in a 250 mL flask. The materials were held at room temperature, from about 20° C. to about 26° C. The conversion of the COCl terminal groups of the AdCL to esters occurred almost immediately and the reaction was permitted to proceed for about 2 hours. NMR on the resulting mixture showed the presence of —CH(CH3)—O—CO— groups (peak at 5.05 ppm) and —CH2—O—CO— groups (peak at 4.2 ppm). The pH of the resulting mixture was very acidic, less than about 1.

About 1 gram of chitosan flakes (medium molecular weight from Aldrich) were added to the mixture with stirring at about 500 rpm and a vacuum was applied. The reaction was allowed to proceed for about 60 to about 72 hours. After this time the pH of the reaction mixture had risen to about 4, which indicates that the chitosan may have been acting as an HCl scavenger.

The resulting material, a PEG/PPG-adipate was then subjected to filtration by applying vacuum suction and the material recovered thereby was subjected to Gel Permeation Chromatography on an Agilent 1100 series LC system equipped with two detectors: an LS Wyatt DAWNHELEOS and RI Wyatt OPTILAB® rEX, and 2 linear columns including a PL gel 10 μm mixed BLS. The material was also subjected to Nuclear Magnetic Resonance (NMR) imaging on a Bruker 300 MHz spectrospin NMR (from Bruker Corporation). The GPC results demonstrated a Mw of about 3108 and a Mn of 2390. NMR data confirmed the ester structure of PEG/PPG-adipate and the presence of end hydroxyl groups.

Derivatization procedures were conducted with trichloroacetylisocyanate, leading to urethane formation with end-hydroxyl groups, which resulted in two shifts: a peak at 4.45 ppm for methylene protons in the urethane bond with the PEG end, and a peak at 5.2 ppm for the methyl proton from the PPG end. This derivatization procedure confirmed the presence of hydroxyl end-groups. The condensation of the polyethylene glycol/polypropylene glycol copolymer with AdCI in bulk occurred without the addition of solvents or catalysts.

Example 2

About 234.15 grams of PEG 600 (Sigma Aldrich, St. Louis, Mo.) was added to a clean 200 mL single neck flask. A stir bar was placed in the flask with PEG 600, the flask was placed in an oil bath at a temperature of about 65° C., and nitrogen gas was bubbled through the PEG 600 for about 1 hour while mixing at a rate of about 200 rpm. This mixing and bubbling with nitrogen was permitted to continue for a period of time of from about 12 hours to about 24 hours. The temperature of the oil bath was reduced to about 30° C. during this time period after the heating at about 65° C. for 1 hour.

The PEG 600 was then added to a 500 mL 3 neck flask fitted with an addition funnel. Static nitrogen was connected to the addition funnel. The exit of an oil bubbler was connected to a large trap with aqueous NaOH. The flask was chilled to a temperature of about 10° C. by placing it in a water/ice bath. About 35.71 grams of adipoyl chloride (AdCI) was added to the PEG 600 dropwise through the addition funnel at a rate of about 30 to about 60 drops per minute. The addition of AdCI took from about 30 to about 40 minutes. The bath was removed and the reaction mixture was stirred for about 20 minutes. The flask was then placed in an oil bath set at a temperature of about 45° C. and nitrogen was bubbled through the reaction mixture with stirring for a period of time from about 16 to about 24 hours. A portion of the resulting material was dissolved in tap water and had a pH of about 5.

The reaction was monitored in situ by infrared spectroscopy using a ReactIR™ 4000 Spectrometer (Mettler-Toledo AutoChem, Columbia, Md.); the ReactIR probe was inserted into one of the necks of the three neck flask; the background utilized was air. The IR spectral spectrometer scans confirmed the formation of PEG-adipate by the presence of an ester peak at 1735 $nm^{-1}$.

About 95 grams of the resulting material was poured into another flask and dissolved in about 115 grams of tetrahydrofuran (THF) (J T Baker, Phillipsburg, N.J.). Once dissolved, the resulting material was precipitated in about 900 mL of diethyl ether. After from about 3 to about 7 minutes of mixing, the material was decanted into a 250 mL 3 neck flask. Nitrogen gas was bubbled through the material without mixing, in order to remove some of the ethyl ether. The resulting material was then dried for a period of time from about 60 to about 72 hours in a vacuum oven. Prior to any sampling, it was determined that about 60 grams of material remained, for a yield of from about 60% to about 70%.

From about 130 to 140 grams of material remained in the original 500 mL flask. This material was dissolved in about 575 grams of anhydrous THF and then transferred to a 1L flask. To this solution about 85 grams of neutral alumina (from Sigma Aldrich, St. Louis, Mo.) was added and mixed for about 45 minutes. The resulting combination was subjected to filtration using pressure filter system from Cole-Parmer Instrument Co. (Vernon Hills, Ill.) equipped with 0.45 mm Fluoropore FHLP filter from Millipore Corporation (Billerica, Mass.).

The filtrate was concentrated on a ROTAVAPOR® rotary evaporator (BÜCHI Labortechnik AG, Flawil, Switzerland). Approximately 500 ml of THF was removed, after which about 250 mL of the remaining material was precipitated in about 1.2 liters of diethyl ether. The material was decanted and transferred to a 500 mL 3 neck flask and then dried for a period of time from about 60 to about 72 hours in a vacuum oven. About 94 grams of product remained after drying, for a yield of from about 65% to about 70%.

The resulting material, a PEG adipate, was subjected to Gel Permeation Chromatography and Nuclear Magentic Resonance imaging utilizing the apparatus described above in Example 1. The GPC results demonstrated Mw of about 2903 and Mn of about 2342. NMR data confirmed the ester structure of PEG-adipate (peak at 4.2 ppm for —$CH_2$—O—CO—) and the presence of hydroxyl end-groups. Derivatization with trichloroacetylisocyanate, leading to urethane formation with hydroxyl end-groups, resulted in a shift at 4.45 ppm. This peak was for methylene protons in the urethane bond with PEG-hydroxyl end-groups.

The condensation of the PEG 600 with AdCI in bulk occurred without the addition of solvents or catalysts.

Example 3

A PEG-adipate similar to the one produced in Example 2 was prepared at a molar ratio of PEG to adipate of about 3:2.

About 202.15 grams of PEG 600 (Sigma Aldrich, St. Louis, Mo.) was added to a clean, 1 liter, 3-neck flask. About 41.1 grams of adipoyl chloride was placed in a graduated addition funnel. The flask was attached to the ReactIR™ 4000 Spectrometer (Mettler-Toledo AutoChem, Columbia, Md.) and the addition funnel was attached to a source of static Nitrogen. The exit of an oil bubbler was connected to a secondary bubbler possessing an aqueous NaOH solution. The flask was chilled to a temperature of about 10° C. by placing it in a water/ice bath. The adipoyl chloride was added to the PEG 600 dropwise through the addition funnel at a rate of about 60 drops per minute with rapid mixing of the material at about 200 rpm. The flask was kept in the ice bath for the first five minutes. The complete addition of the adipoyl chloride took from about 30 to about 35 minutes. The bath was removed and the reaction mixture was stirred for about 45 minutes. The flask was then placed in an oil bath set at a temperature of about 45° C. and mixed with a mechanical stirrer at about 200 rpm. Nitrogen was bubbled through the reaction mixture with stirring for a period of time from about 16 to about 24 hours. The reaction was monitored in situ by infrared spectroscopy using a ReactIR™ 4000 Spectrometer (Mettler-Toledo AutoChem, Columbia, Md.); the ReactIR probe was inserted into one of the necks of the three neck flask; the background utilized was air.

About 197 grams of the resulting material was then transferred to a 1 liter flask. About 815 mL of tetrahydrofuran (THF) and about 140 grams of neutral alumina (from Sigma Aldrich, St. Louis, Mo.) was added to the flask. Mixing occurred at a rate of about 900 rpm with a stir bar for from about 2 to about 2.25 hours. The resulting combination was subjected to filtration using pressure filter system from Cole-Parmer Instrument Co. (Vernon Hills, Ill.) equipped with 0.5 μm Millipore filter from Millipore Corporation (Billerica, Mass.).

The filtrate was concentrated on a ROTAVAPOR® rotary evaporator (BÜCHI Labortechnik A G, Flawil, Switzerland). Approximately 400 mL of the remaining material was precipitated in about 1.2 liters of diethyl ether. The material was mixed with the stir bar for about 15 minutes and then decanted and transferred to a tared 500 mL 3 neck flask and then dried for a period of time from about 12 to about 24 hours in a vacuum oven.

The resulting material, a PEG adipate, was subjected to Nuclear Magnetic Resonance imaging utilizing the apparatus described above in Example 1. The NMR data confirmed the ester structure of PEG-adipate (peak at 4.2 ppm for —$CH_2$—O—CO—) and the presence of hydroxyl end-groups. The molecular weight of the material was about 2610, as determined from the NMR results.

About 124.5 grams of product remained after drying, which was added to about 50.3 grams of 4,4'-methylene bis (phenyl isocyanate) MDI).

The flask was then placed under static nitrogen in an oil bath at a temperature of about 65° C. Once the material in the flask had melted, the contents were stirred at about 150 rpm for 4.5 hours. The temperature was then decreased to about 58° C. The resulting material, an isocyanate functional PEG adipate, was washed with petroleum ether 7 times and the flask was then placed under a vacuum.

The isocyanate functionalized PEG adipate thus produced was then dried overnight, for a period of time from about 12 hours to about 24 hours, after which about 48.12 grams of the material was added to a 250 mL 2-neck flask. About 0.133 grams of trimethylol propane (TMP) was added to the flask, which was then placed in an oil bath at a temperature of about 65° C. under static nitrogen and stirred at a rate of about 50 rpm. The material was left in the bath for about 72 hours and degassed for about 30 minutes prior to placement in syringes.

The resulting adhesive material was tested for NCO content by titration and found to have about 3.67% NCO. The adhesive material was also subjected to a lap shear test using porcine stomach. Briefly, the lap shear test was conducted as follows. Room temperature porcine stomach tissue was cut into 15×45 mm pieces using a punch. The tissue was rinsed with saline and blotted to remove excess moisture. About 200 mg of the adhesive material was applied to the end of one of the tissue pieces. The adhesive material was spread to cover an area of about 15×15 mm at one edge of the tissue piece. An edge of another tissue piece was placed on top of the area covered by the adhesive so that the two tissue pieces extended in opposite directions, with the adhesive located between the two overlapping edges.

A 20 gram weight was placed on top of the adhered area for about 30 seconds. The weight was removed and the adhesive was let cure for about 4.5 minutes more, for a total of about 5 minutes cure time. The free end of one of the tissue pieces was placed into a grounding clamp, while the free end of the other tissue piece was placed into a clamp mounted on a counter. A force meter was attached to the top clamp and the force required to pull the pieces apart was recorded.

The results of the lap shear test showed the material had a lap shear of about 1462 grams at 5 minutes.

Example 4

About 959.1 grams of polyethylene glycol having a molecular weight of about 600 (PEG 600) was added to a clean, dry 3000 mL 4 neck flask. The flask had a mechanical stirring assembly, was under a nitrogen blanket, and was kept at a temperature of about 65° C. The PEG 600 was added to the reaction flask via a vacuum adapter and equilibrated with stirring at about 400 revolutions per minute (rpm) while maintained at about 65° C. The PEG 600 was dried by bubbling nitrogen through the material overnight, from about 16 to about 24 hours. The temperature of the flask was reduced to about 20° C.

About 146.2 grams of adipoyl chloride was added to a clean, dry 250 mL addition funnel. The addition funnel was attached to the reaction flask and the adipoyl chloride therein was added to the PEG 600 at a rate of from about 60 to about 80 drops per minute, until all of the adipoyl chloride had been added. After about 2.5 hours, the temperature was increased from about 20° C. to about 45° C., followed by bubbling nitrogen through the material overnight, from about 16 to about 24 hours.

The temperature of the reaction flask was then decreased to about 20° C., at which time about 1.5 liters of tetrahydrofuran (THF) was added to the reactor and stirred to dissolve the contents of the reactor, which occurred after about 10 minutes. The solution obtained was then transferred to a clean 4 liter Erlenmeyer flask and about 0.5 liters of THF was added.

The solution thus obtained was pumped through an alumina-filled column having about 1,235 grams of alumina at a rate of about 60 mL/minute to about 70 mL/minute, followed by passage through a pressure filter. After all the solution had passed through the column, about 1 liter of fresh THF was passed through the column. The filtered solution was concentrated on a ROTOVAPOR® rotary evaporator (BÜCHI Labortechnik AG, Flawil, Switzerland) to obtain a solution having a volume of about 1 liter.

About 600 mL of diethyl ether was then added to the concentrated solution and shaken vigorously. The ether was decanted, and the process was repeated with the addition of more ether and shaking. The ether was again decanted and the solution was returned to the ROTOVAPOR® rotary evaporator to remove some of the remaining ether, at which time the product, a PEG adipate, was placed in glass jars and dried under vacuum.

Example 5

About 40 grams of p-phenylene diisocyanate (PDI) was added to a 250 ml single neck flask. About 170 grams of toluene was added and the flask was placed under static nitrogen on an oil bath at about 50° C. After about 4 hours, the flask was removed from the oil bath and the contents of the flask were filtered with filter paper. The clear solution obtained was rotaovapped to dryness on a ROTOVAPOR® rotary evaporator. The material was rinsed with petroleum ether and was placed in a vacuum oven for about 72 hours.

Approximately 90.53 grams of PEG adipate from Example 4 above was combined with about 16.5 grams of the purified PDI described above in a 250 ml 3 neck flask. The flask was placed in an oil bath at a temperature of about 75° C. under static nitrogen at a mixer speed of about 150 rpm and mixed for about 4 hours. The temperature was reset to about 40° C. and mixing continued for another 90 minutes.

About 56.475 grams of the resulting material was then transferred to a 100 ml 2 neck flask. About 0.353 grams of TMP was added to the material. The flask was placed in an oil bath at a temperature of about 65° C. under static nitrogen at a mixer speed of about 50 rpm. After about 25 hours, the reaction was stopped and the resulting branched material was transferred to 30 cc syringes.

A lap shear test was conducted on this material as described above in Example 3; the lap shear at 5 minutes was about 1605 grams. NCO content was determined by titration as described above in Example 3 and the material was found to have about 3.125% NCO. The molecular weight of the material was about 4387.

It will be appreciated that various of the above-disclosed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims. Unless specifically recited in a claim, steps or components of claims should not be implied or imported from the specification or any other claims as to any particular order, number, position, size, shape, angle, color, or material.

What is claimed is:

1. A solvent-free, catalyst-free method for producing a biocompatible composition comprising:

contacting a polyalkylene oxide having a molecular weight from about 200 to about 1000 with an aliphatic dicarboxylic acid for a period of time from about 0.5 hours to about 120 hours to form a mixture;

stirring the mixture in the presence of an inert gas and an acid scavenger selected from the group consisting of chitosan, neutral alumina, basic alumina, activated charcoal, and combinations thereof, for a period of time from about 1 hour to about 72 hours, at a temperature of from about 20° C. to about 75° C., to adjust the pH of the mixture to a pH from about 3 to about 7;

maintaining the mixture at a temperature from about −70° C. to about 85° C., and recovering a flowable aliphatic polyester macromer from the mixture, wherein the molar ratio of polyalkylene oxide to aliphatic dicarboxylic acid is from about 4:3 to about 2:1.

2. The method of claim 1, wherein the polyalkylene oxide is selected from the group consisting of polyethylene oxide, polypropylene oxide, block copolymers of polyethylene oxide and polypropylene, and random copolymers of polyethylene oxide and polypropylene oxide.

3. The method of claim 1, wherein the polyalkylene oxide is selected from the group consisting of polyethylene glycol and polyethylene glycol/polypropylene glycol copolymers.

4. The method of claim 3, wherein the polyethylene glycol possesses a molecular weight of from about 400 to about 900.

5. The method of claim 3, wherein the polyethylene glycol/polypropylene glycol copolymer possesses about 17 moles polyethylene glycol to about 6 moles polypropylene glycol.

6. The method of claim 1, wherein the aliphatic dicarboxylic acid is selected from the group consisting of sebacic acid, azelaic acid, suberic acid, pimelic acid, adipic acid, glutaric acid, succinic acid, malonic acid, oxalic acid and combinations thereof.

7. The method of claim 1, wherein the aliphatic dicarboxylic acid comprises a derivative of the aliphatic dicarboxylic acid selected from the group consisting of oxalyl chloride, malonyl chloride, succinyl chloride, glutaryl chloride, adipoyl chloride, suberoyl chloride, pimeloyl chloride, sebacoyl chloride, and combinations thereof.

8. A solvent-free, catalyst-free method for producing a biocompatible composition comprising:

contacting a polyalkylene oxide having a molecular weight from about 200 to about 1000 with an aliphatic dicarboxylic acid for a period of time from about 0.5 hours to about 120 hours to form a mixture;

stirring the mixture in the presence of an inert gas and an acid scavenger selected from the group consisting of chitosan, neutral alumina, basic alumina, activated charcoal, and combinations thereof, for a period of time from about 1 hour to about 72 hours, at a temperature of from about 20° C. to about 75° C., to adjust the pH of the mixture to a pH from about 3 to about 7;

maintaining the mixture at a temperature from about −70° C. to about 85° C., and recovering a flowable aliphatic polyester macromer from the mixture: wherein the molar ratio of polyalkylene oxide to aliphatic dicarboxylic acid is from about 4:3 to about 2:1;

contacting the aliphatic polyester macromer with a first isocyanate selected from the group consisting of aromatic, aliphatic and alicyclic diisocyanates, to produce an isocyanate end-capped aliphatic polyester macromer; and reacting the isocyanate end-capped aliphatic polyester macromer with a polyol to produce a polyurethane as the biocompatible composition.

9. The method of claim 8, further comprising reacting the polyurethane with a second isocyanate to produce an isocyanate-functional polyurethane as the biocompatible composition.

10. The method of claim 8, wherein the polyalkylene oxide is selected from the group consisting of polyethylene glycol and polyethylene glycol/polypropylene glycol copolymers, the aliphatic dicarboxylic acid is selected from the group consisting of sebacic acid, azelaic acid, suberic acid, pimelic acid, adipic acid, glutaric acid, succinic acid, malonic acid, oxalic acid and combinations thereof, and the first isocyanate is selected from the group consisting of 2,4-toluene diisocyanate, 2,6-toluene diisocyanate, 2,2'-diphenylmethane diisocyanate, 2,4'-diphenylmethane diisocyanate, 4,4'-diphenylmethane diisocyanate, diphenyidimethylmethane diisocyanate, dibenzyl diisocyanate, naphthylene diisocyanate, phenylene diisocyanate, xylylene diisocyanate, 4,4'-oxybis(phenylisocyanate), tetramethylxylylene diisocyanate, tetramethylene diisocyanate, hexamethylene diisocyanate, dimethyl diisocyanate, lysine diisocyanate, 2-methylpentane-1,5-diisocyanate, 3-methylpentane-1,5-diisocyanate or 2,2,4-trimethylhexamethylene diisocyanate, isophorone diisocyanate, cyclohexane diisocyanate, hydrogenated xylylene diisocyanate, hydrogenated diphenylmethane diisocyanate, hydrogenated trimethylxylylene diisocyanate, 2,4,6-trimethyl 1,3-phenylene diisocyanate, and combinations thereof.

11. The method of claim 8, wherein the step of reacting the aliphatic polyester macromer with the first diisocyanate further comprises heating the aliphatic polyester macromer and the diisocyanate at a temperature of from about 40° C. to about 140° C.

12. The method of claim 8, wherein the polyol is selected from the group consisting of ethylene glycol, diethylene glycol, triethylene glycol, polyethylene glycol, polyethylene glycol adipate, propylene glycol, dipropylene glycol, polypropylene glycol, tetraethylene glycol, 1,3-butanediol, 1,4-butanediol, 1,2,4-butanetriol, glycerol, trimethylol propane, 1,2,5-hexanetriol, 1,2,6-hexanetriol, polycaprolactone triol, polylactide triol, 4,4'-dihydroxyphenylpropane, 4,4'-dihydroxyphenylmethane, bis(hydroxyethyl)terephthalate, cyclohexane dimethanol, furan dimethanol, pentaerythritol, glucose, sucrose, sorbitol, polyethylene oxide-polypropylene oxide copolymers, and combinations thereof.

13. The method of claim 9, wherein the second isocyanate is selected from the group consisting of 2,4-toluene diisocyanate, 2,6-toluene diisocyanate, 2,2'-diphenylmethane diisocyanate, 2,4'-diphenylmethane diisocyanate, 4,4'-diphenylmethane diisocyanate, diphenyidimethylmethane diisocyanate, dibenzyl diisocyanate, naphthylene diisocyanate, phenylene diisocyanate, xylylene diisocyanate, 4,4'-oxybis(phenylisocyanate), tetramethylxylylene diisocyanate, tetramethylene diisocyanate, hexamethylene diisocyanate, dimethyl diisocyanate, lysine diisocyanate, 2-methylpentane-1,5-diisocyanate, 3-methylpentane-1,5-diisocyanate or 2,2,4-trimethylhexamethylene diisocyanate, isophorone diisocyanate, cyclohexane diisocyanate, hydrogenated xylylene diisocyanate, hydrogenated diphenylmethane diisocyanate, hydrogenated trimethylxylylene diisocyanate, 2,4,6-trimethyl 1,3-phenylene diisocyanate, and combinations thereof.

14. The method of claim 8, wherein reacting the isocyanate end-capped aliphatic polyester macromer with the polyol further comprises heating the isocyanate end-capped aliphatic polyester macromer and the polyol at a temperature of from about 40° C. to about 100° C.

15. The method of claim 9, wherein reacting the polyurethane with the second isocyanate further comprises heating the polyurethane and the second isocyanate to a temperature of from about 40° C. to about 140° C.

16. A biocompatible composition made by the process of claim 8, wherein the composition does not possess solvent residues or catalyst residues.

17. A biocompatible composition made by the process of claim 9, wherein the composition does not possess solvent residues or catalyst residues.

18. The method of claim 1, wherein the polyalkylene oxide and the aliphatic dicarboxylic acid are contacted for a period of time from about 0.5 hours to about 5 hours, and stirring the mixture occurs for a period of time from about 12 hours to about 24 hours at a temperature from about 30° C. to about 60° C.

* * * * *